(12) United States Patent
Kim

(10) Patent No.: US 12,376,983 B2
(45) Date of Patent: Aug. 5, 2025

(54) ORTHOTIC ARCH SUPPORT DEVICES AND METHODS OF USE

(71) Applicant: Richard Kim, Gansevoort, NY (US)

(72) Inventor: Richard Kim, Gansevoort, NY (US)

( * ) Notice: Subject to any disclaimer, the term of this patent is extended or adjusted under 35 U.S.C. 154(b) by 0 days.

(21) Appl. No.: 17/805,854

(22) Filed: Jun. 7, 2022

(65) Prior Publication Data

US 2022/0370230 A1    Nov. 24, 2022

Related U.S. Application Data

(63) Continuation-in-part of application No. 16/029,090, filed on Jul. 6, 2018, now Pat. No. 11,350,699.

(51) Int. Cl.
*A61F 5/14*    (2022.01)
*A43B 7/14*    (2022.01)

(52) U.S. Cl.
CPC .............. *A61F 5/14* (2013.01); *A43B 7/1495* (2013.01)

(58) Field of Classification Search
CPC ..... A43B 7/1495; A43B 7/1405; A43B 7/141; A43B 7/142; A43B 7/14; A43B 7/22; A43B 17/02; A43B 17/023; A43B 17/14; A61F 5/14
USPC ...................................................... 36/43, 91
See application file for complete search history.

(56) References Cited

U.S. PATENT DOCUMENTS

| | | | |
|---|---|---|---|
| 717,523 A | 1/1903 | Arrowsmith | |
| 984,140 A * | 2/1911 | Hughes ................. | A43B 7/142 36/158 |
| 1,853,998 A | 4/1932 | Sadler | |
| 2,043,396 A * | 6/1936 | Schnellbacher ....... | A43B 7/223 36/158 |
| 2,943,405 A * | 7/1960 | Olson .................... | A43B 7/142 36/173 |
| 3,339,555 A * | 9/1967 | Rotko ................... | A43B 7/1468 36/165 |
| 4,441,499 A * | 4/1984 | Comparetto ......... | A43B 7/1415 36/154 |
| 5,224,277 A | 7/1993 | Sang Do | |
| 5,311,680 A | 5/1994 | Comparetto | |
| 5,903,985 A | 5/1999 | DeMarchi | |

(Continued)

FOREIGN PATENT DOCUMENTS

| | | |
|---|---|---|
| CN | 1182559 | 5/1998 |
| CN | 1232653 | 10/1999 |

(Continued)

OTHER PUBLICATIONS

International Search Report and Written Opinion of the International Searching Authority for PCT/US2019/040651, Jan. 29, 2020, 15 pages.

(Continued)

*Primary Examiner* — Aiying Zhao
(74) *Attorney, Agent, or Firm* — Heslin Rothenberg Farley & Mesiti P.C.; Jacquelyn A. Graff, Esq.

(57) ABSTRACT

Orthotic devices for providing arch support for the foot are disclosed. The orthotic device includes a base member, an arch support portion, and a covering for coupling the arch support portion to the base member. A method of providing continuous contact with the plantar surface of the foot during all phases of the gait cycle is also disclosed. In addition, methods of assembling and using the orthotic device are also disclosed.

13 Claims, 13 Drawing Sheets

(56) References Cited

U.S. PATENT DOCUMENTS

| | | | |
|---|---|---|---|
| 6,105,283 A | 8/2000 | Park | |
| 6,345,455 B1 | 2/2002 | Greer, Jr. | |
| 6,510,626 B1 | 1/2003 | Greenawalt | |
| 6,976,322 B1 * | 12/2005 | Walker | A43B 7/223 36/43 |
| 7,430,820 B2 | 10/2008 | Andreoli | |
| 7,770,309 B2 * | 8/2010 | Scofield | A43D 999/00 36/165 |
| 8,745,894 B2 | 6/2014 | Cheskin | |
| 9,345,286 B2 | 5/2016 | Holt | |
| 2008/0127526 A1 | 6/2008 | Spicer | |
| 2008/0313927 A1 | 12/2008 | Conforti | |
| 2009/0071038 A1 | 3/2009 | Luthi | |
| 2009/0265956 A1 | 10/2009 | Richards | |
| 2010/0005566 A1 | 1/2010 | Gabe | |
| 2010/0064550 A1 * | 3/2010 | Kahn | A43B 17/02 36/165 |
| 2010/0269375 A1 | 10/2010 | Georgoulakis | |
| 2011/0288446 A1 | 11/2011 | Hsieh | |
| 2011/0302805 A1 * | 12/2011 | Vito | A43B 7/1464 36/145 |
| 2012/0246971 A1 | 10/2012 | Donzis | |
| 2012/0317843 A1 | 12/2012 | Bove | |
| 2017/0055629 A1 | 3/2017 | Schickling | |
| 2017/0099907 A1 | 4/2017 | Cin | |
| 2017/0258176 A1 | 9/2017 | Waatti et al. | |
| 2019/0021438 A1 * | 1/2019 | Salkavich | A43B 7/144 |

FOREIGN PATENT DOCUMENTS

| | | |
|---|---|---|
| CN | 101083921 | 12/2007 |
| CN | 101801228 | 8/2010 |
| DE | 19603755 | 8/1997 |
| DE | 202009015388 | 12/2010 |
| EP | 0409101 | 1/1991 |
| EP | 0464000 | 1/1992 |
| JP | 10127305 | 5/1998 |
| JP | 10127305 A * | 5/1998 |
| KR | 100755029 | 9/2007 |
| WO | 1997041747 | 11/1997 |
| WO | 1998052435 | 11/1998 |
| WO | 2007037581 | 4/2007 |
| WO | 2015112471 | 7/2015 |
| WO | 2016191505 | 12/2016 |

OTHER PUBLICATIONS

CS&E PCT Collaborative Search and Examination Pilot Upload Peer Contribution in International Patent Application No. PCT/US2019/040651, Peer ISA—Korean Intellectual Property Office (KIPO), Sep. 24, 2019, 17 pages.

CS&E PCT Collaborative Search and Examination Pilot Upload Peer Contribution in International Patent Application No. PCT/US2019/040651, Peer ISA—China National Intellectual Property Administration (CNIPA), Sep. 19, 2019, 11 pages.

CS&E PCT Collaborative Search and Examination Pilot Upload Peer Contribution in International Patent Application No. PCT/US2019/040651, Peer ISA—European Patent Office (EPO), Sep. 26, 2019, 12 pages.

CS&E PCT Collaborative Search and Examination Pilot Upload Peer Contribution in International Patent Application No. PCT/US2019/040651, Peer ISA—Japan Patent Office (JPO), Sep. 19, 2019, 9 pages.

Extended European Search Report issued in European Patent Application No. 19830622.7, Mar. 17, 2022, 7 pages.

English Translation of Examination Report issued in Chinese Patent Application No. 201980045403.9, Jan. 20, 2023, 20 pages.

* cited by examiner

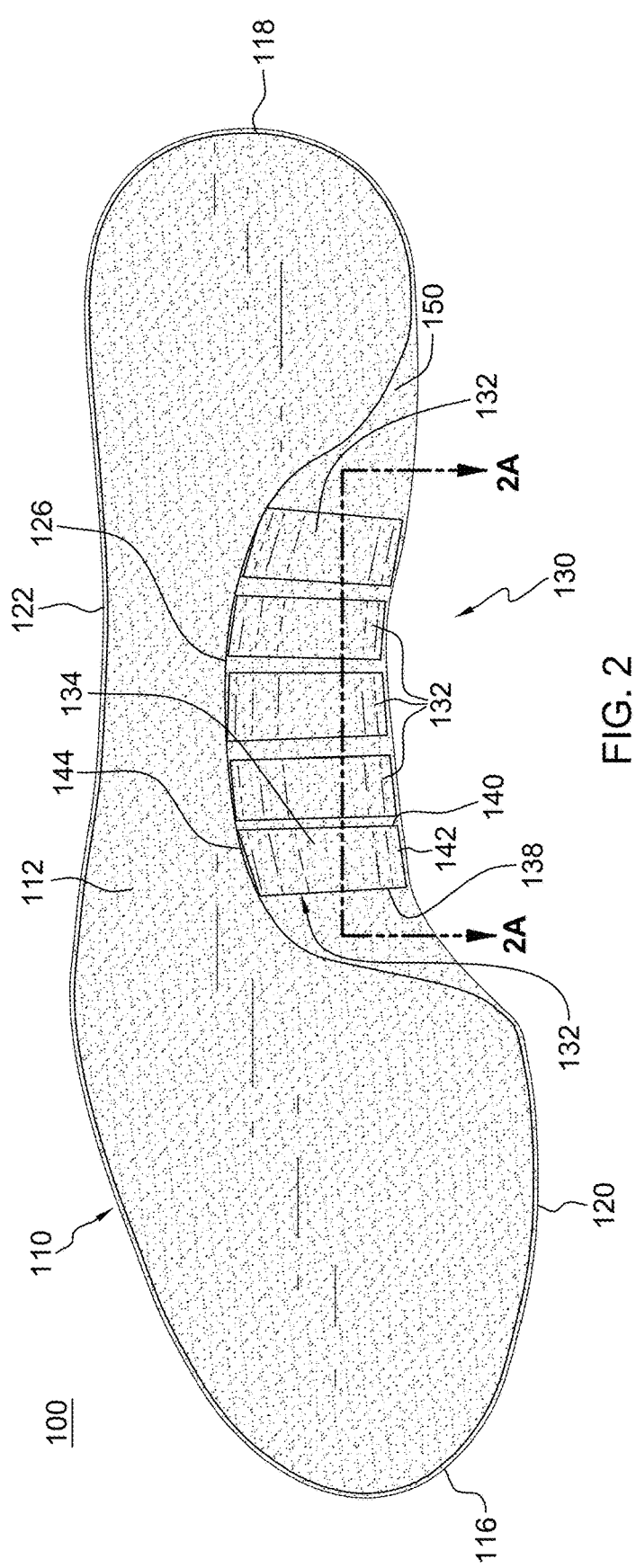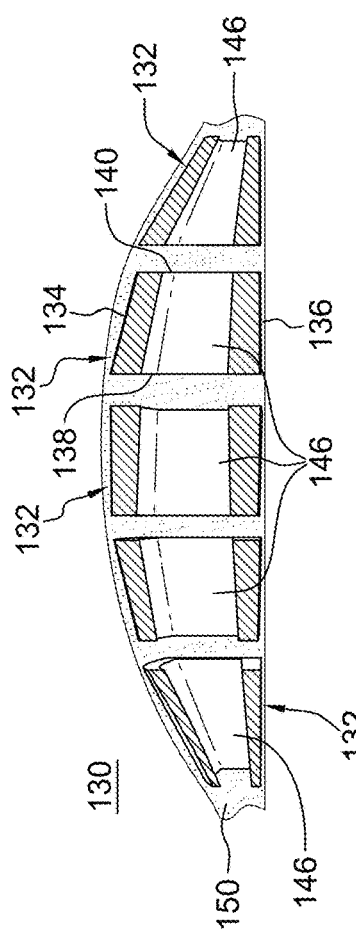

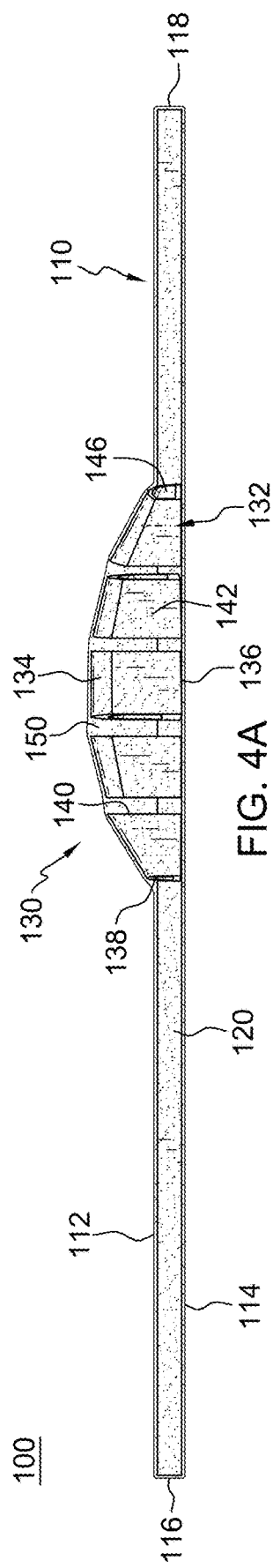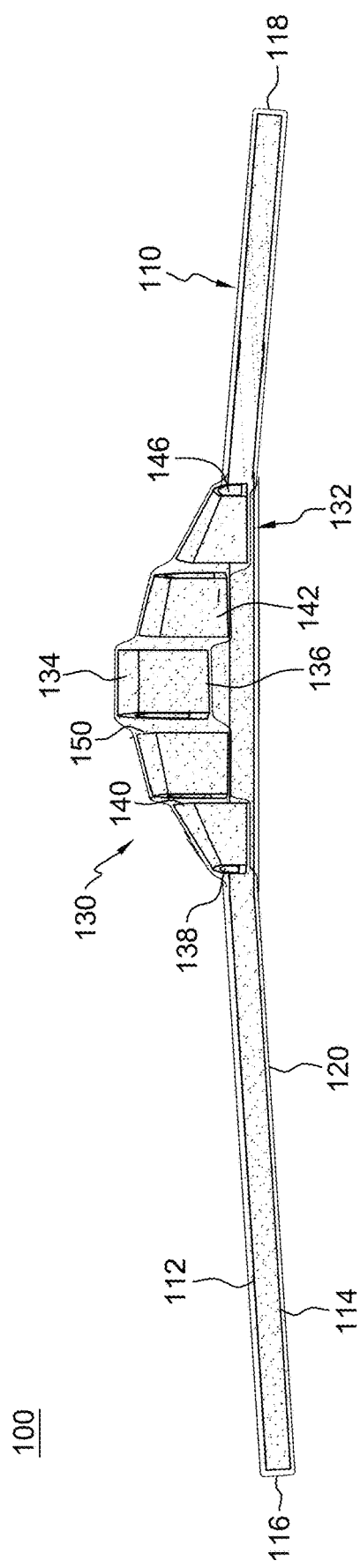

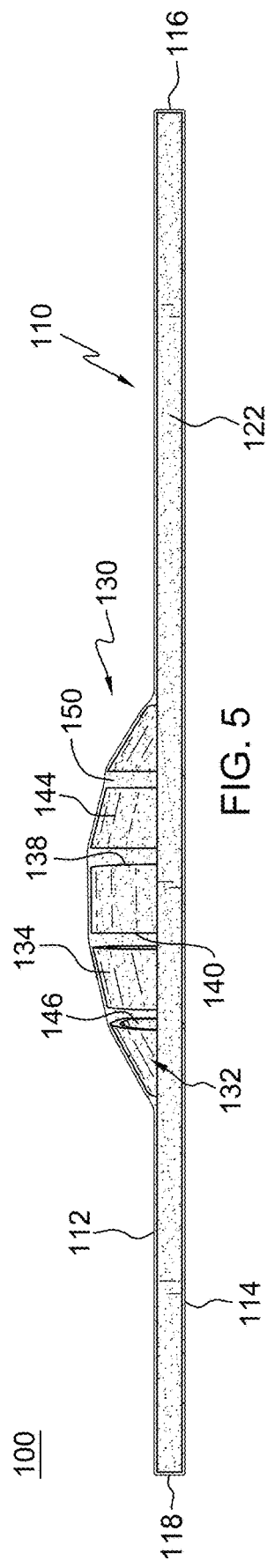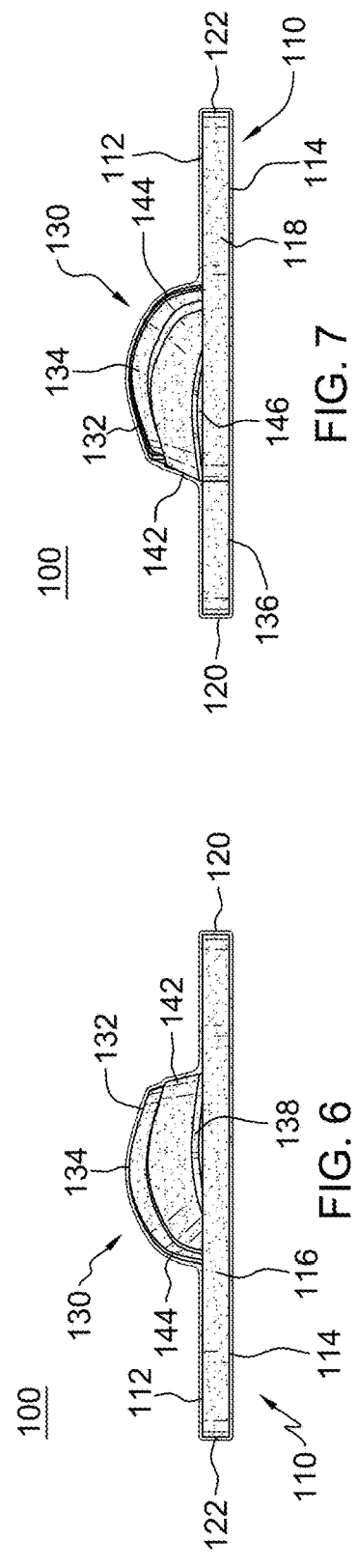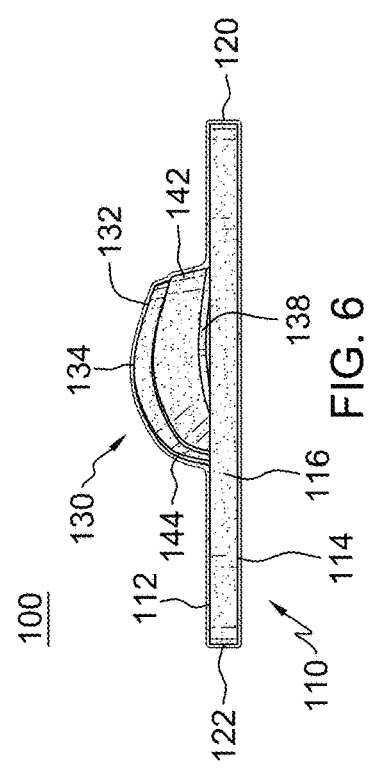

ORTHOTIC ARCH SUPPORT DEVICES AND METHODS OF USE

CROSS REFERENCE TO RELATED APPLICATION

This application is a continuation-in-part of U.S. application Ser. No. 16/029,090 filed on Jul. 6, 2018 and entitled Orthotic Arch Support Device and Method of Use, which issues as U.S. Pat. No. 11,350,699 on Jun. 7, 2022, which is hereby incorporated by reference in its entirety.

TECHNICAL FIELD

The present disclosure relates generally to the podiatric, orthopedic, orthotic and footwear fields related to providing arch support for the foot. More specifically, but not exclusively, the present disclosure relates to devices and methods for providing continuous contact with the plantar surface of the foot during all phases of the gait cycle.

BACKGROUND OF THE INVENTION

Most solutions for providing arch support are either rigid and provide a structured system without foot flexibility or flexible and unable to provide plantar support. Device that are rigid and/or uniform are adept to stationary activities, such as, standing, but do not provide support when the user is active as they remain linear to the plantar aspect of the foot. Flexible or softer insole devices allow for increased flexibility, but do not provide sufficient plantar and arch support. Thus, new and improved arch support devices and methods for using the devices are needed to provide both foot and sole flexibility while also providing increased plantar and arch support.

SUMMARY OF THE INVENTION

The present disclosure is directed toward devices and methods for providing continuous contact with the plantar surface of the foot during all phases of the gait cycle.

In one aspect of the present disclosure provided herein, is an orthotic device. The orthotic device including a base member, an arch support portion, and a covering coupling the arch support portion to the base member.

In another aspect of the present disclosure provided herein, is a method of assembling an orthotic device. The method includes obtaining a plurality of arch members. The method also includes positioning the plurality of arch members within a covering. Finally, the method includes coupling the covering containing the plurality of arch members to the base member.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

FIG. 2 is a dorsal view of the orthotic device of FIG. 1, in accordance with an aspect of the present disclosure;

FIG. 2A is a cross-sectional view taken along line 2A-2A in FIG. 2, in accordance with an aspect of the present disclosure;

FIG. 4A is a medial view of the orthotic device of FIG. 1, in accordance with an aspect of the present disclosure;

FIG. 4B is a medial view of the orthotic device of FIG. 1 during a mid-swing stance phase of the gait cycle, in accordance with an aspect of the present disclosure;

FIG. 5 is a lateral view of the orthotic device of FIG. 1, in accordance with an aspect of the present disclosure;

FIG. 6 is a distal view of the orthotic device of FIG. 1, in accordance with an aspect of the present disclosure;

FIG. 7 is a proximal view of the orthotic device of FIG. 1, in accordance with an aspect of the present disclosure;

DETAILED DESCRIPTION FOR CARRYING OUT THE INVENTION

Figure 1:
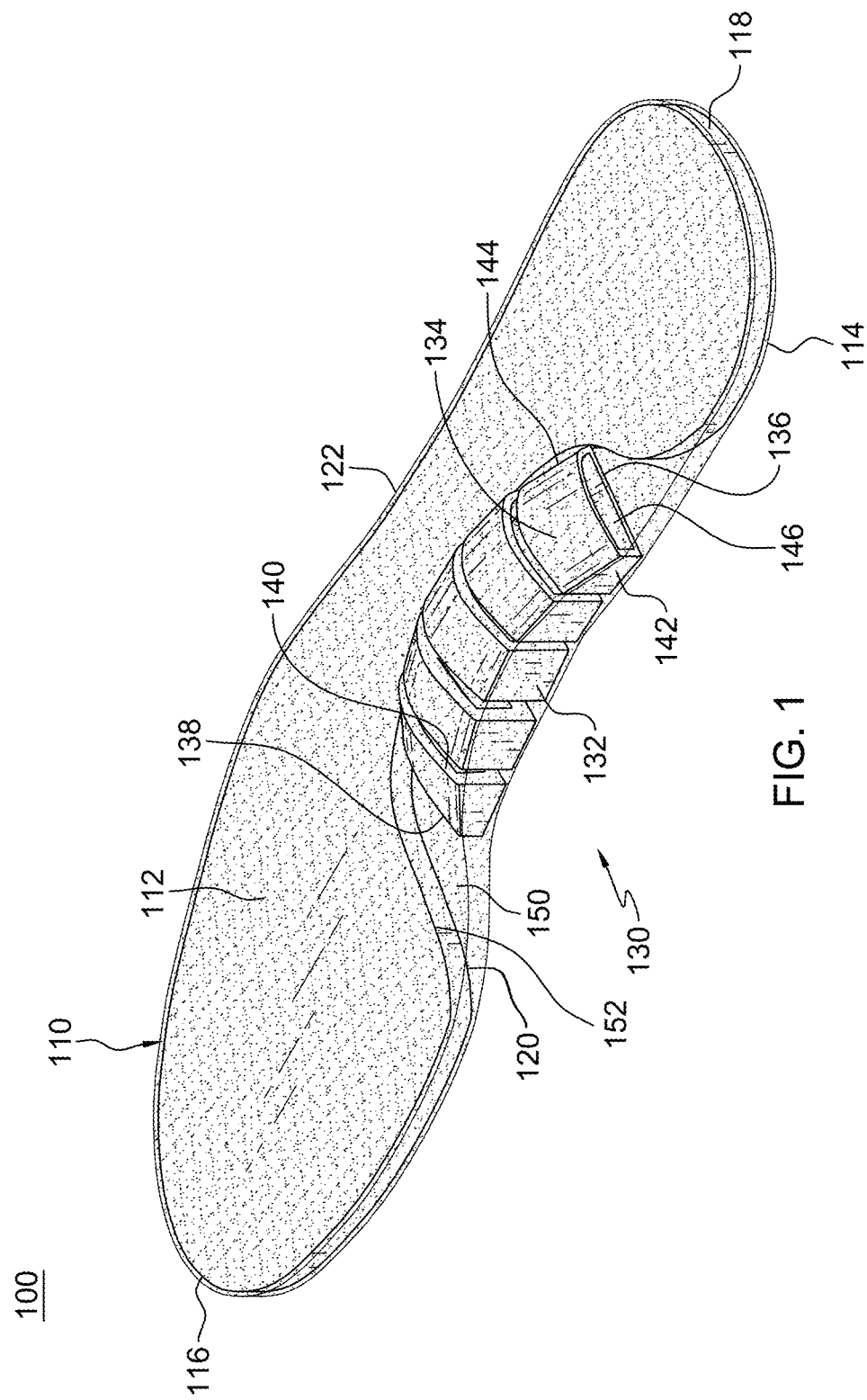
FIG. 1 is a perspective view of one embodiment of an orthotic device, in accordance with an aspect of the present disclosure.

Generally stated, disclosed herein are devices for providing arch support for the foot. Further, methods for using the devices to provide continuous contact with the plantar surface of the foot during all phases of the gait cycle are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device nearest the torso, while "distal" indicates the portion of the device farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices and methods are described herein with reference to use with the bones of the foot, the bones of the foot, ankle and lower leg may be used to describe the surfaces, positions, directions or orientations of the devices and methods. Further, the devices and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices and methods, and the aspects, components, features and the like thereof, described herein with respect to the right foot may be mirrored so that they likewise function with the left foot. Further, the devices and methods, and the aspects, components, features and the like thereof, disclosed herein are described with respect to the foot for brevity purposes, but it should be understood that the devices and methods may be used with other bones of the body having similar structures.

Referring to the drawings, wherein like reference numerals are used to indicate like or analogous components throughout the several views, and with particular reference to FIGS. 1-7, there is illustrated an exemplary embodiment of an orthotic device or arch support 100. The orthotic device 100 includes a base member 110, an arch support portion 130, and a covering 150 to moveably couple the arch support portion 130 to the base member 110.

Figure 3:
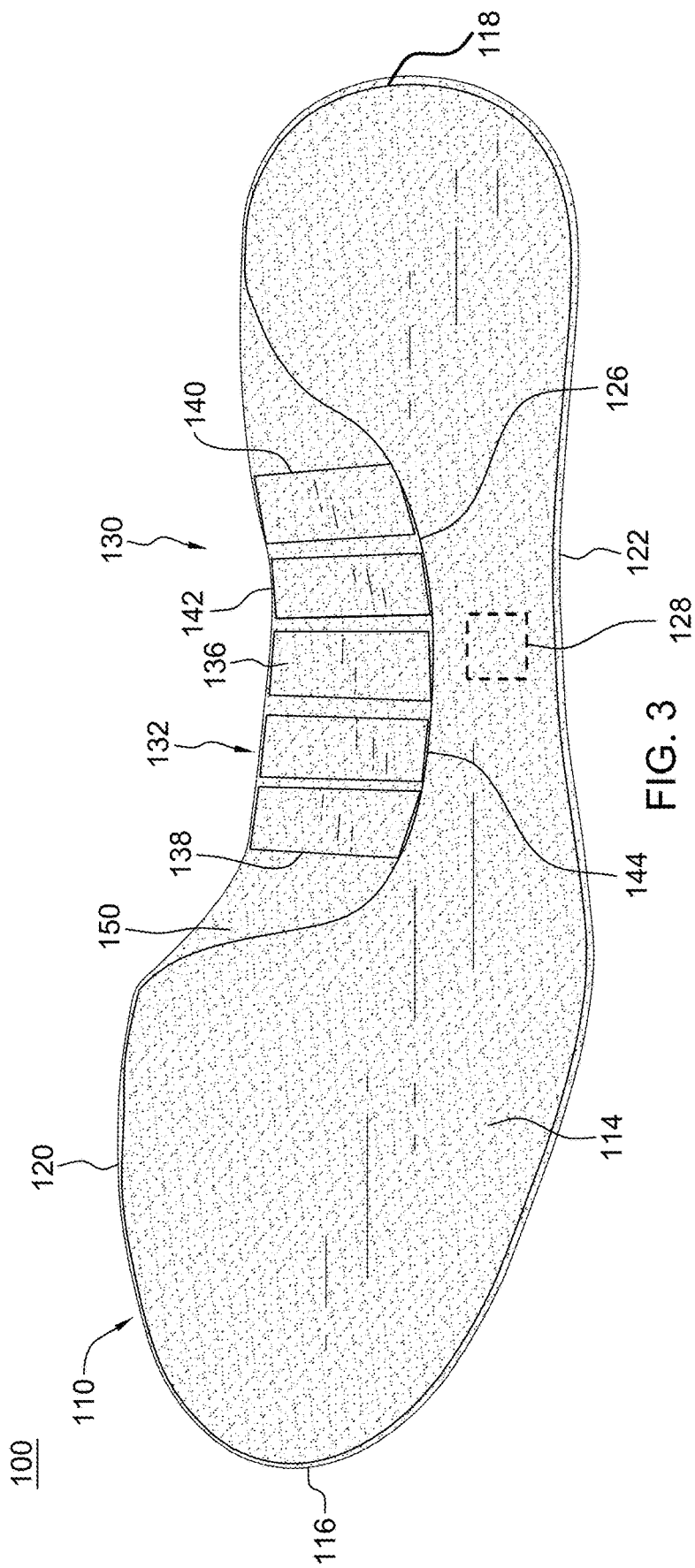
FIG. 3 is a plantar view of the orthotic device of FIG. 1, in accordance with an aspect of the present disclosure.

With continued reference to FIGS. 1-7, the base member 110 includes a top or superior side 112 opposite a bottom or inferior side 114, a first or distal end 116 opposite a second or proximal end 118, and a medial side 120 opposite a lateral side 122. The base member 110 may also include a recessed region 126 extending into the base member 110 from the medial side 120. The recessed region 126 also extends from the superior side 112 of the base member 110 to the inferior side 114 of the base member 110. The distance between the recessed region 126 on the medial side 120 and the lateral side 122 may vary to position the arch support portion 130 in the desired location for a given patient and/or a given anatomical pathology. For example, the distance between the recessed region 126 and the lateral side 122 of the base member 110 may be wider or narrower than shown. The base member 110 may be made of, for example, a soft rubber, flexible silicone, or a like material that provides support and flexibility to the plantar side of the foot. The inferior side 114 of the base member 110 may include, for example, a plurality of members or a textured surface. The plurality of members may be, for example, a plurality of hexagonal or polygonal members that allow the base member 110 to deform and return to shape during a wearer's gait cycle. The plurality of members may also be positioned in a lattice matrix. For purposes of illustration, the plurality of members or textured surface is shown in FIG. 3 as the box labeled reference number 128. Although the box indicating the plurality of members or the textured surface is only shown on a portion of the inferior side 114 near a midpoint of the base member 110 between the first end 116 and second end 118, it is understood by the description herein that the plurality of members, i.e., hexagonal members, polygonal members or lattice matrix, or textured surface may positioned anywhere on the inferior side 114 including on the entire inferior side 114 of the base member 110. The superior side 112 of the base member 110 may be, for example, generally flat with contours that match the shape of the foot of the wearer or alternatively, may be, for example, preformed to address anatomical pathologies of the wearer.

The arch support portion 130 includes a plurality of arch members 132, as shown in FIGS. 1-5. Each arch member 132 of the plurality of arch members 132 is a separate piece, not connected to any other arch member 132 or the base member 110. Each arch member 132 is independent from each other arch member 132 and from the base member 110, such that the covering 150 is the only connection between the arch members 132 and the arch members 132 and the base member 110. As each arch member 132 is an individual piece separate from each other arch member 132, each arch member 132 can move freely with respect to each other arch member 132. Each arch member 132 of the plurality of arch members 132 may include, for example, a top or superior portion 134, a bottom or inferior portion 136, a first or distal end 138, a second or proximal end 140, a medial side 142, and a lateral side 144, as shown in FIGS. 1 and 2A. The superior portion 134 of the arch members 132 may be, for example, arced or curved between the medial side 142 and the lateral side 144 of the arch members 132. The superior portion 134 of the arch members 132 may be, for example, arced or curved in a convex orientation, a concave orientation, or a combination of convex and concave orientations between the medial side 142 and the lateral side 144. The lateral side 144 may also be, for example, arced or curved as it extends between the superior portion 134 and the inferior portion 136 of the arch members 132. The inferior portion 136 may be, for example, relatively planar or flat as it extends between the medial side 120 and the lateral side 122. The medial side 142 may also be, for example, relatively planar or flat as it extends between the superior portion 134 and the inferior portion 136 of the arch members 132. In addition, at least one first arch member 132 may be, for example, tapered in a distal to proximal direction between the first and second ends 138, 140 of the arch member 132, and at least one second arch member 132 may be, for example, tapered in a proximal to distal direction between the first and second ends 138, 140. In an embodiment, the center arch member 132 may be, for example, planar or flat in a proximal-distal direction, i.e., may not be tapered. Although shown as an odd number of arch members 132, i.e., five arch members 132, the arch support portion 130 may have, for example, any number of arch members 132, which may be an odd or even number of arch members 132, as needed to provide continuous contact with the plantar surface of the foot with any given anatomical pathology.

Each arch member 132 may also include an opening or hollow portion 146 extending from the first or distal end 138 to the second or proximal end 140 of each arch member 132. The size and shape of the hollow portion 146 may be selected, for example, to provide the desired support and flexibility for a patient's plantar arch through the entire gait cycle. The edges of the hollow portion 146 of each arch member 132 may form, for example, a rimmed edge around the perimeter of each arch member 132 on the first and second ends 138, 140. The rimmed edge of the arch members 132 may be, for example, rounded, curved, smooth or the like to allow for each arch member 132 to translate with respect to the adjacent arch members 132. The plurality of arch members 132 may be, for example, collated or positioned relative to each other to form the shape of the arch of the foot. For example, the first end 138 of each of the plurality of intermediate arch members 132 and the second end arch member 132 is separate from the second end 140 of each adjacent arch member 132 of the first end arch member 132 and the plurality of intermediate arch members 132. The plurality of arch members 132 may, for example, align in a resting state, as shown in FIGS. 1-7, to form the arch support portion 130 of the orthotic device 100. Alternatively, the arch members 132 may be, for example, offset such that they are positioned in a non-linear planar orientation, as needed to provide continuous contact with the plantar surface of the wearer's foot. The arch members 132 may be positioned in a non-linear planar orientation whereby the bottom surfaces of the arch members 132 are positioned different distances from a plane extending from the bottom surface of the base member 110. For example, the plurality of arch members 132 includes a first end arch member 132, a plurality of intermediate arch members 132, and a second end arch member 132 with the first end 138 of each intermediate arch member 132 of the plurality of arch members 132 and the second end arch member 132 is positioned next to the second end 140 of the first end arch member 132 and each adjacent intermediate arch member 132 of the plurality of arch members 132 in a first position and each arch member 132 of the plurality of arch members 132 is positioned at least partially overlapping each adjacent arch member 132 of the plurality of arch members 132 in a second position. The adjacent surfaces of each arch member 132 may, for example, be partially overlapping along a superior-inferior direction of the orthotic device 100, such that the bottom surfaces of the arch members 132 form arc shapes during the various stages of the gate cycle. In addition, the planes of each arch member 132 may be, for example, positioned generally perpendicular to the recessed region 126 of the base member 110, or alternatively, the planes of each arch member 132 may be, for example, positioned at varying angles relative to the recessed region 126 of the base member 110. The position of the planes of each arch member 132 relative to the recessed region 126 of the base member 110 may be selected to provide continuous contact with the plantar surface of the wearer's foot for a given anatomical pathology. The arch support portion 130 may be, for example, semi-flexible. The arch members 132 may be, for example, made of slices of plastic or a like material that provide the desired support for the arch of a patient's foot and also the desired flexibility to move during the gait cycle.

As shown in FIGS. 1-3, the lateral side 144 of each arch member 132 is positioned separate from and adjacent to the medial side 120 of the base member 110 in a recessed region 126. The arch members 132 may, for example, directly contact at least a portion of the medial side 120 of the base member 110 or be spaced apart from the base member 110. The arch members 132 may also be positioned to correspond to the position of a patient's foot arch when the plantar side of the foot contacts the base member 110. The arch members 132 may also be positioned, for example, at the most lateral portion of the arch. The arch members 132 may be, for example, coupled to or secured to the base member 110 by a covering 150, such as an elastic covering or deformable covering 150. For example, each arch member 132 of the plurality of arch members 132 is completely separated from each other arch member 132 of the plurality of arch members 132 when contained within the covering 150. The covering 150 may be secured to the base member 110 by, for example, coupling or sealing the covering 150 to a rim (not shown) of the base member 110. The covering 150 may be, for example, sealed into a rubber rim on the medial side or edge 120 of the base member 110 and the rim may be inset into the base member 110. For illustration purposes, the location of the rim on the medial side or edge 120 in the recessed region is shown as reference number 152. The covering 150 surrounds or encases the arch members 132 to retain order and shape of the arch support portion 130. For example, at least a portion of the covering 150 is sealed to the rim 152 of the base member 110 positioned in the recessed region 126 of the base member 110 forming a first cover portion extending from the superior side 112 of the base member 110 across the top portion 134 of the arch members 132, a second cover portion extending from the top portion 134 of the arch members 132 to the bottom portion 136 of the arch members 132, and a third cover portion extending across the bottom portion 136 of the arch members 132 to the inferior side 114 of the base member 110. The first cover portion, the second cover portion, and the third cover portion create an opening for the plurality of arch members 132 to be surrounded by the covering 150. The covering 150 also allows for the arch members 132 to form the arch support portion 130 of the orthotic device 100 and also to move with respect to the other arch members 132. In addition, the covering 150 may allow for the arch members 132 to overlap with the adjacent arch members 132 as the shape of the foot arch changes during a person's gait cycle. The covering 150 may be made of, for example, an elastic fabric material or another material that stretches and is flexible.

A method of using the orthotic device 100 is also disclosed. The method includes the plurality of arch members 132 aligning to provide consistent segmental pressure to the arch, primarily, the plantar fascia, during the flat foot and mid stance phase of the gait cycle. Next, during the heel off and toe off phases of the gait cycle, the plurality of arch members 132 slide past the neighboring or adjacent arch members 132 based on the flexion of the foot and the shape change of the sole providing contiguous pressure to the arch/plantar fascia. In this heel off and toe off phase, each arch member 132 of the plurality of arch members 132 is positioned at least partially overlapping each adjacent arch member 132 of the plurality of arch members in a second position. Then, during the mid-swing stance phase of the gait cycle, the plurality of arch members 132 remain in an overlapped arrangement to provide equal segmental pressure to the arch/plantar fascia. Next, during the heel strike phase of the gait cycle, the individual arch members 132 again slide past neighboring or adjacent arch members 132 corresponding to the change in shape of the sole providing contiguous pressure on the arch/plantar fascia. Finally, during the flat foot and mid stance phase of the gait cycle, the plurality of arch members 132 realign to allow the plurality of arch members 132 to repeat the movement cycle.

Figure 8:
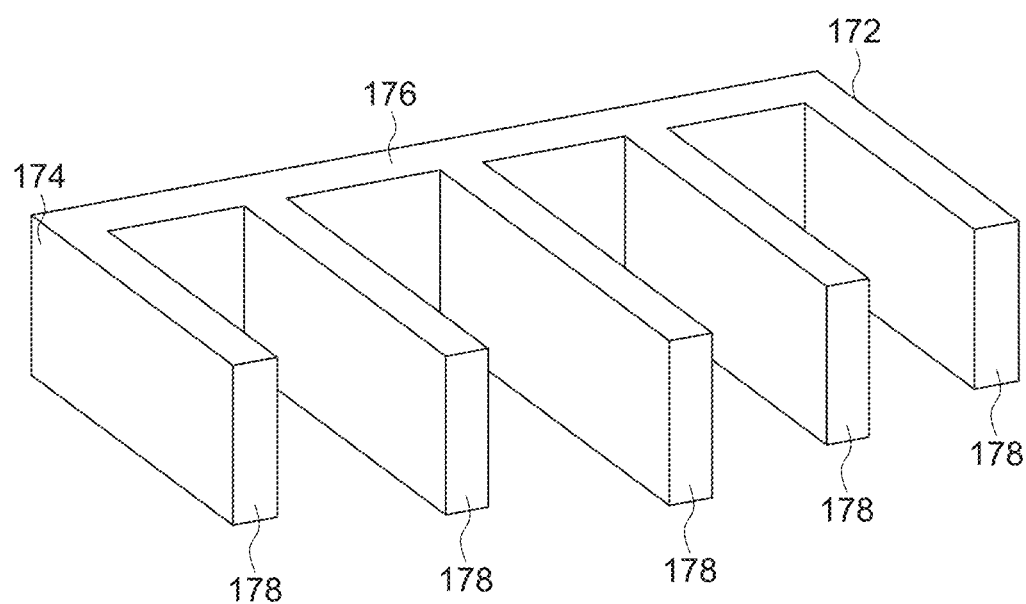
FIG. 8 is a perspective view of a guide portion of another arch support portion of the orthotic device of FIG. 1, in accordance with an aspect of the present disclosure.
Figure 9:
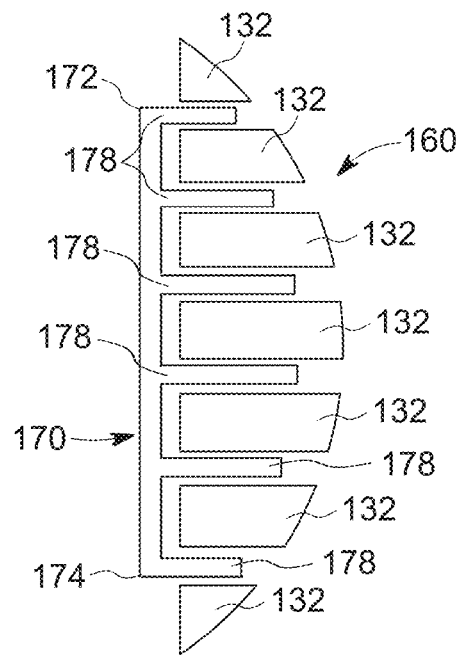
FIG. 9 is a superior view of the guide portion of FIG. 8 inserted into an arch support portion, in accordance with an aspect of the present disclosure.
Figure 10:
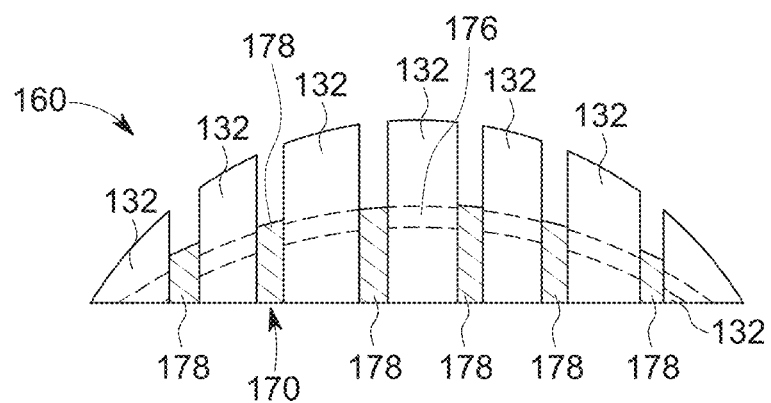
FIG. 10 is a lateral view of a curved base member of the guide portion of FIG. 8 inserted into an arch support portion, in accordance with an aspect of the present disclosure.

Referring now to FIGS. 8-10, an alternative arch support portion 160 is shown. The arch support portion 160 includes a plurality of arch members 132 and a guide portion 170. The arch members 132 are as described above with reference to arch support portion 130 and will not be described again here for brevity's sake. The arch support portion 160 may include a plurality of arch members 132 that include, for example, approximately three to seven arch members 132, however, more than seven arch members 132 are also contemplated for larger feet. The guide portion 170 may be, for example, coupled to the base member 110 of the orthotic device 100 with the covering 150. The guide portion 170 may be secured to the covering 150 and the covering 150 may be coupled to the base member 110 to secure the guide portion 170 relative to the base member 110. The arch members 132 may also be secured within the covering 150, as discussed in greater detail above and which will not be discussed again here for brevity's sake. In addition, the arch members 132 are secured within the covering 150 in order for the arch members 132 to be positioned relative to the guide portion 170, such that the arch members 132 translate relative to the guide portion 170. Alternatively, the guide portion 170 may be, for example, coupled to the base member 110 of the orthotic device 100 at a first end 172 and at a second end 174.

With continued reference to FIGS. 8-10, the guide portion 170 includes a base member 176 and a plurality of extensions 178. At least a portion of each arch member 132 is received between two adjacent extensions 178 to provide a guide or track for the motion of the arch members 132 during the gait cycle. The base member 176 extends between the first end 172 and the second end 174 of the guide portion 170. The base member 176 may be, for example, planar, curved in a convex direction, or curved in a concave direction to match or correspond to the medial surface of the arch members 132. The base member 176 may be positioned only on the medial side of the plurality of arch members 132, as shown in FIG. 9. The plurality of extensions 178 are spaced along the length of the base member 176. The space between each extension 178 may be, for example, approximately the same width as the arch member 132 to be positioned between each set of extensions 178. The width is measured, for example, along a proximal to distal direction between the toe and heel of the orthotic device 100. Each extension 178 may have the same length or different lengths extending away from the base member 176 of the guide portion 170. The intermediate extensions 178 may be, for example, longer than the extensions 178 at the first end 172 or second end 174 of the guide portion 170. In addition, the extensions 178 may be, for example, the same length as the shortest adjacent arch member 132 or shorter than the length of the shortest adjacent arch member 132. Although the FIGS. 8-10 show the guide portion 170 with angled edges, it is also contemplated that the edges may be curved, smooth, arced or otherwise shaped to reduce irritation with the user's foot.

Figure 11:
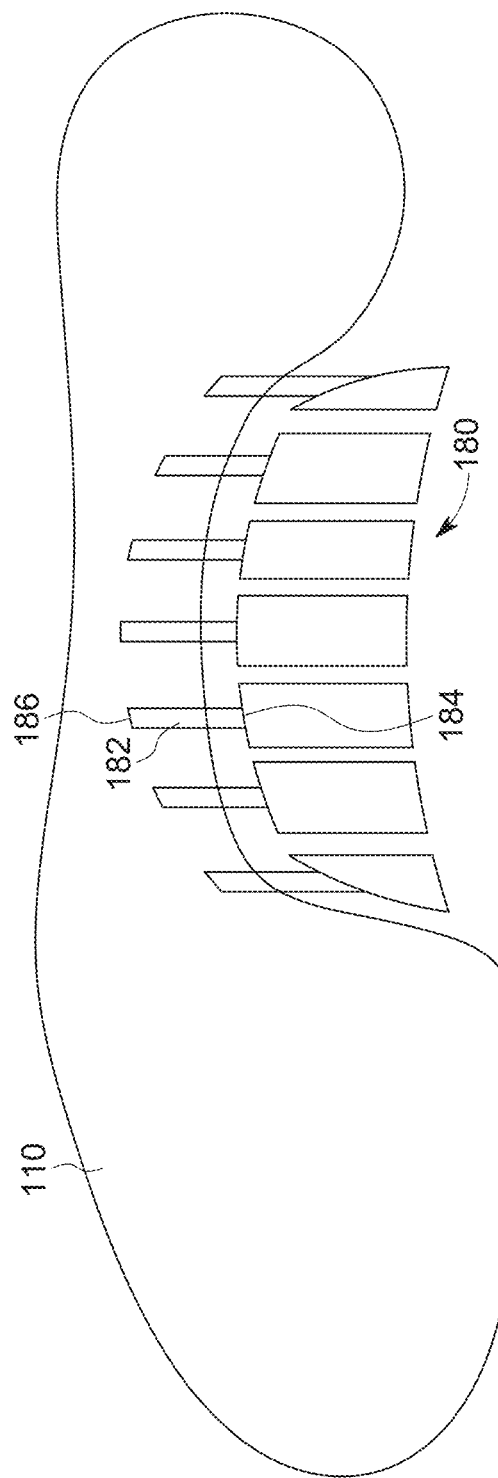
FIG. 11 is a superior view of another arch support portion of the orthotic device of FIG. 1 with lateral arch attachments connecting the arch members to the base member, in accordance with an aspect of the present disclosure.

Referring now to FIG. 11, another arch support portion 180 of the orthotic device 100 is shown. The arch support portion 180 includes a plurality of arch members 132 and lateral arch attachments or connectors 182 connecting each of the arch members 132 to the base member 110. Each connector 182 includes a first end 184 coupled to the lateral side 144 of each arch member 132 and a second end 186 coupled to the base member 110 of the orthotic device 100. Each connector 182 includes a width, for example, that is smaller than the width of the coupled arch member 132. In addition, each connector 182 includes a length to maintain each arch member 132 positioned within the recessed region 126 of the orthotic device 100. The second end 186 of each connector 182 may include a flat tongue or widened region (not shown) for securement to the base member 110. The tongue of the second end 186 may be, for example, embedded into the base member 110 between the top side 112 and the bottom side 114 of the base member 110. It is also contemplated that tongue of the second end 186 may be, for example, coupled to the top side 112 or the bottom side 114 of the base member 110. The connectors 182 are flexible and allow for each arch member 132 to move during the gait cycle while limiting stray motion of the arch members 132 and preventing disordering of the arch segments 132. The arch support portion 180 may be, for example, used with or without the covering 150.

Figure 12:
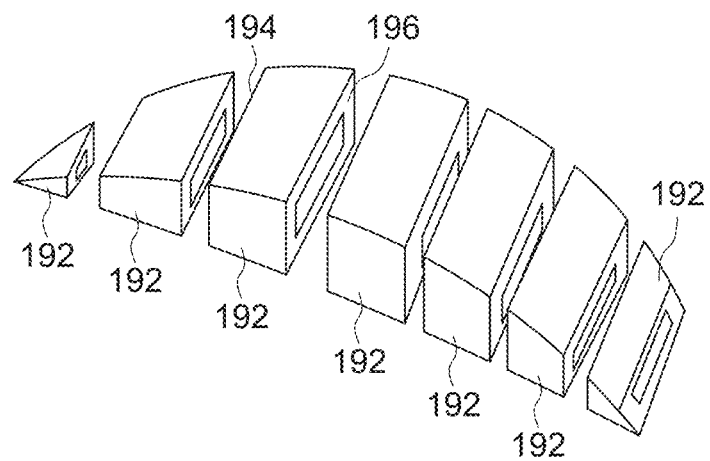
FIG. 12 is a perspective view of another embodiment of the arch support portion of the orthotic device of FIG. 1, in accordance with an aspect of the present disclosure.
Figure 13A:
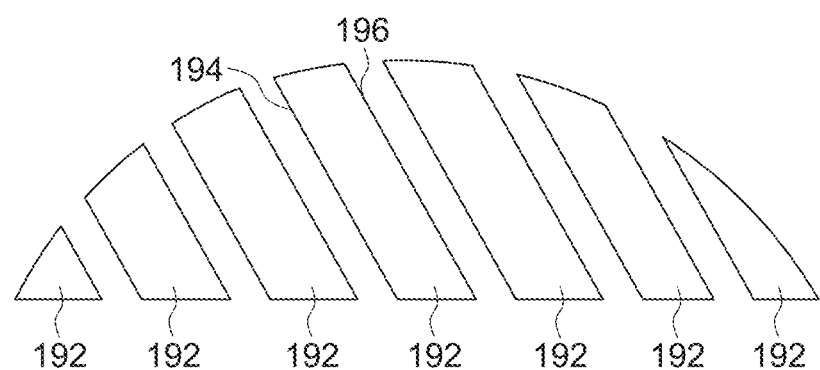
FIG. 13A is a superior view of the arch support portion of FIG. 12, in accordance with an aspect of the present disclosure.
Figure 13B:
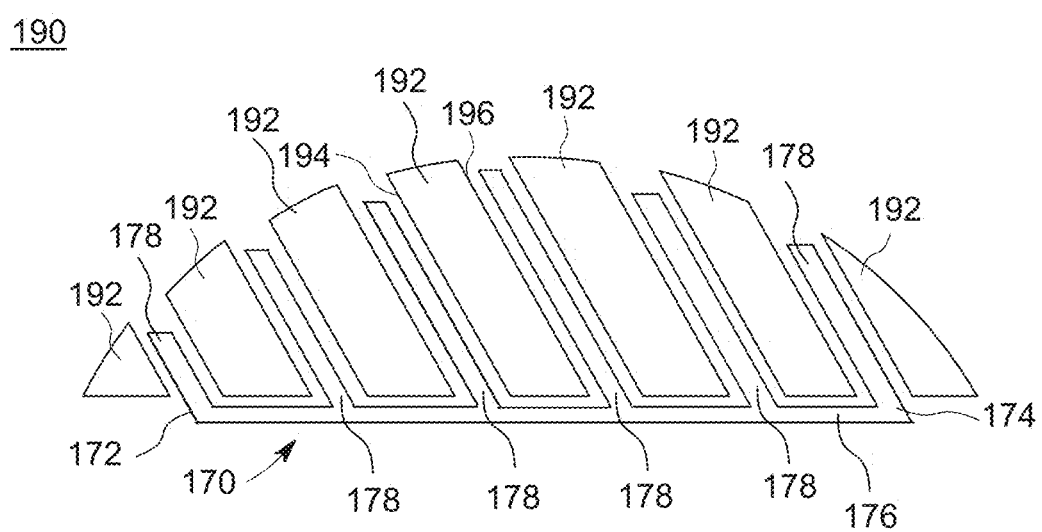
FIG. 13B is a superior view of the arch support portion of FIG. 13A with a guide portion inserted into the arch support portion, in accordance with an aspect of the present disclosure.

Yet another arch support portion 190 of the orthotic device 100 is shown in FIGS. 12- 13B. The arch support portion 190 includes a plurality of arch members 192. Each arch member 192 of the plurality of arch members 192 may include, for example, a top or superior portion 134, a bottom or inferior portion 136, a first or distal end 194, a second or proximal end 196, a medial side 142, and a lateral side 144, as shown in FIG. 12. The superior portion 134, the inferior portion 136, the medial side 142, and the lateral side 144 are the same or similar to as described above with reference to FIGS. 1-7 and will not be described again here for brevity's sake. The first end 194 and the second end 196 may be, for example, angled between the medial sides 142 and the lateral sides 144 of each arch member 192. As the arch members 192 extend from the base member 110, the arch members 192 extend away at an angle relative to a longitudinal axis of the base member 110 extending between the first end 116 and the second end 118. The first and second ends 194, 196 of the arch members 192 may have a number of different angles to form the arch support portion 190. The angles of the arch members 192 may be selected, for example, to provide improved direct support to a user's arch during the various phases of the gait cycle. The arch support portion 190 may be, for example, coupled to the base member 110 with or without the covering 150. If the arch support portion 190 is used without the covering 150, then a guide portion similar to guide portion 170 having angled extensions 178, as shown in FIG. 13B, or the connectors 182 could be used to couple the arch members 192 to the base member 110.

Figure 14:
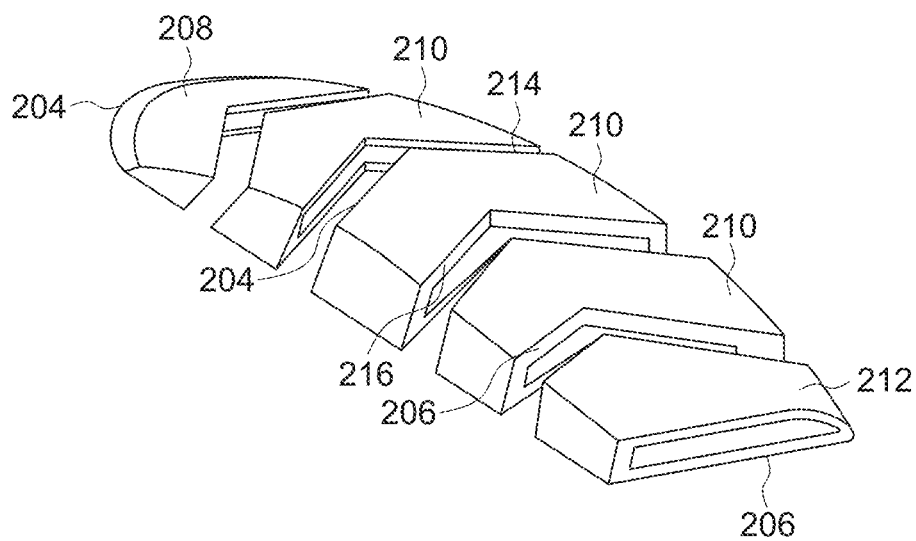
FIG. 14 is perspective view of another arch support portion of the orthotic device of FIG. 1 with five arch members, in accordance with an aspect of the present disclosure.
Figure 15:
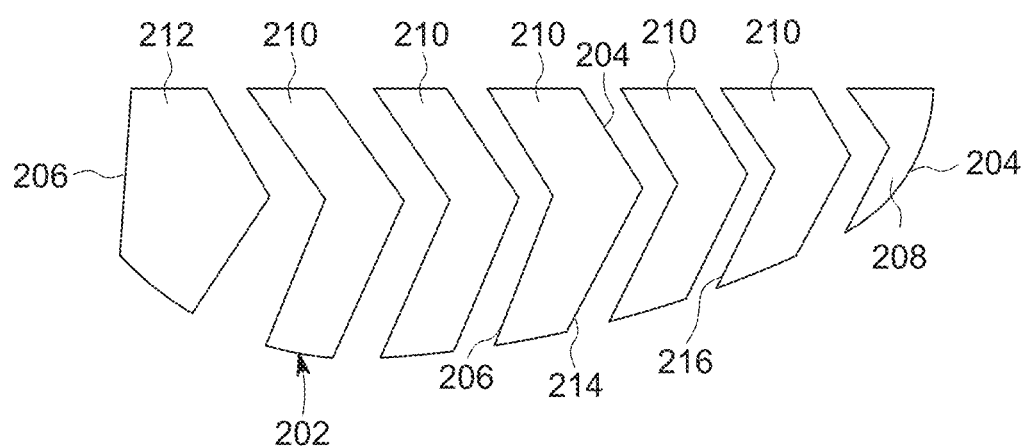
FIG. 15 is a superior view of an embodiment of the arch support portion of FIG. 14 with seven arch members, in accordance with an aspect of the present disclosure.

Referring now to FIGS. 14-15, an arch support portion 200 of the orthotic device 100 is shown. The arch support portion 200 includes a plurality of arch members 202. Each arch member 208, 210, 212 of the plurality of arch members 202 may include, for example, a top or superior portion 134, a bottom or inferior portion 136, a first or distal end 204, a second or proximal end 206, a medial side 142, and a lateral side 144, as shown in FIG. 14. The superior portion 134, the inferior portion 136, the medial side 142, and the lateral side 144 are the same or similar to as described above with reference to FIGS. 1-7 and will not be described again here for brevity's sake. The first end 204 and the second end 206 may include, for example, corresponding protrusions 214 and grooves 216, respectively, on all intermediate first and second ends 204, 206. More specifically, the first end arch member 208 includes a groove 216 on the second end 206, while the second end arch member 212 includes a protrusion 214 on the first end 204. Each of the intermediate arch members 210 includes both a protrusion 214 on the first end 204 and a groove 216 on the second end 206. Each adjacent protrusion 214 and groove 216 pair share a corresponding shape to engage each other to assist with limiting stray motion of the arch members 202 and prevent any potential disordering of the arch members 202. Thus, as each arch member 202 moves during a gait cycle, the protrusions 214 and grooves 216 of adjacent arch members 202 may engage each other to allow for the arch members 202 to engage and maintain their position relative to each other as they translate in a superior-inferior direction. The arch support portion 200 may be, for example, coupled to the base member 110 with or without the covering 150. If the arch support portion 200 is used without the covering 150, then a guide portion similar to guide portion 170 having angled extensions 178 or the connectors 182 could be used to couple the arch members 202 to the base member 110.

Figure 16:
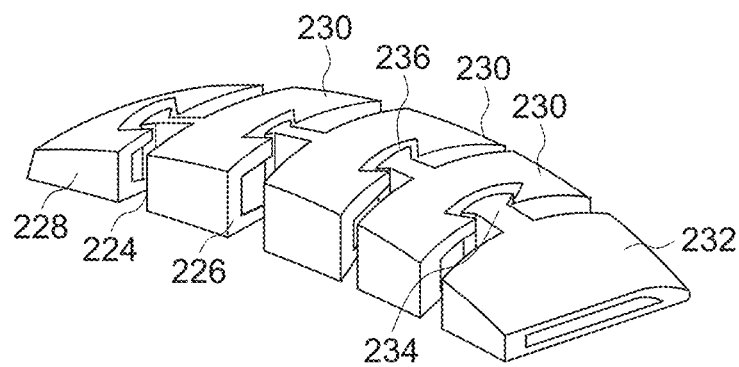
FIG. 16 is a perspective view of another arch support portion of the orthotic device of FIG. 1 with five arch members, in accordance with an aspect of the present disclosure.
Figure 17:
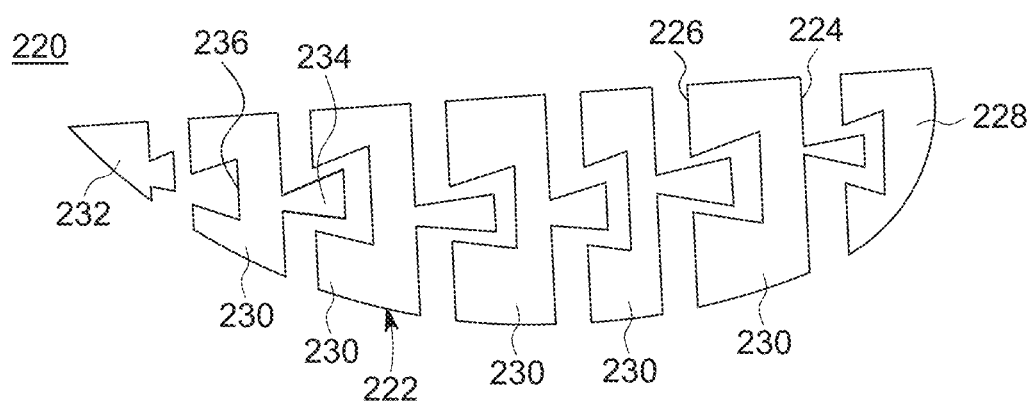
FIG. 17 is a superior view of an embodiment of the arch support portion of FIG. 16 with seven arch members, in accordance with an aspect of the present disclosure.

Referring now to FIGS. 16-17, another arch support portion 220 of the orthotic device 100 is shown. The arch support portion 220 includes a plurality of arch members 222. Each arch member 228, 230, 232 of the plurality of arch members 222 may include, for example, a top or superior portion 134, a bottom or inferior portion 136, a first or distal end 224, a second or proximal end 226, a medial side 142, and a lateral side 144, as shown in FIG. 16. The superior portion 134, the inferior portion 136, the medial side 142, and the lateral side 144 are the same or similar to as described above with reference to FIGS. 1-7 and will not be described again here for brevity's sake. The first end 224 and the second end 226 may include, for example, corresponding protrusions 234 and grooves 236, respectively, on all intermediate first and second ends 224, 226. More specifically, the first end arch member 228 includes a groove 236 on the second end 226, while the second end arch member 232 includes a protrusion 234 on the first end 224. Each of the intermediate arch members 230 includes both a protrusion 234 on the first end 224 and a groove 236 on the second end 226. Each adjacent protrusion 234 and groove 236 pair share a corresponding shape to engage each other to assist with limiting stray motion of the arch members 222 and prevent any potential disordering of the arch members 222. Thus, as each arch member 222 moves during a gait cycle, the protrusions 234 and grooves 236 of adjacent arch members 222 may engage each other to allow for the arch members 222 to engage and maintain their position relative to each other as they translate in a superior-inferior direction. The arch support portion 220 may be, for example, coupled to the base member 110 with or without the covering 150. If the arch support portion 220 is used without the covering 150, then a guide portion similar to guide portion 170 having angled extensions 178 or the connectors 182 could be used to couple the arch members 222 to the base member 110. The protrusion 234 may have, for example, a triangular shape, as shown, or alternatively, another shape where the end coupled to the arch member 222 is smaller than the free end of the arch member 222. Likewise, the groove 236 may have, for example, a triangular shape, as shown, or alternatively, another shape where the interior portion of the grove 236 is larger than the opening of the groove 236 on the exterior surface of the arch member 222.

Figure 18:
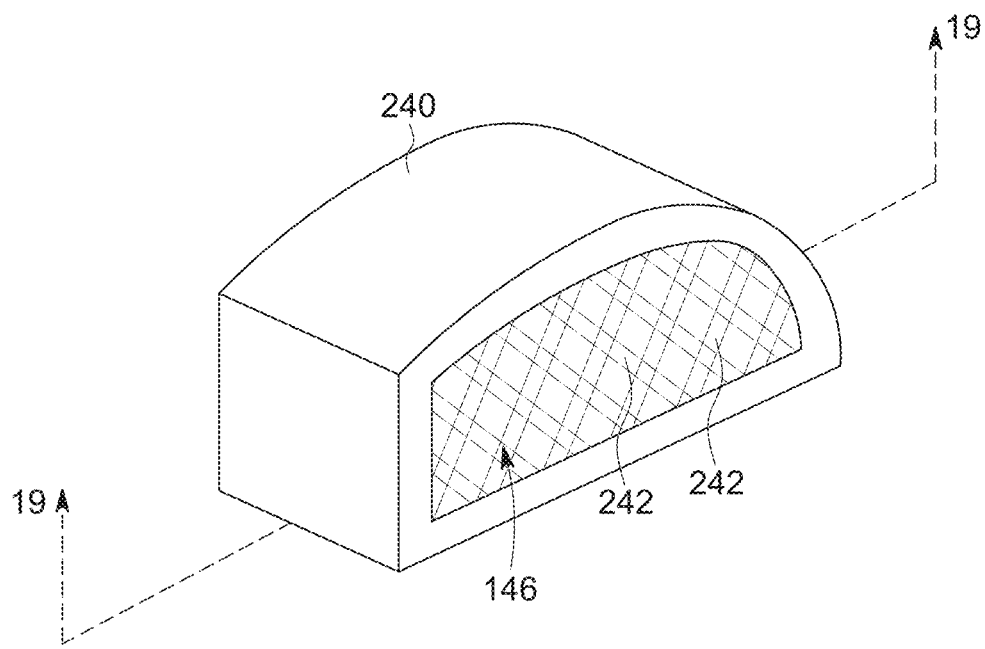
FIG. 18 is a perspective view of an arch member of the orthotic device of FIG. 1, in accordance with an aspect of the present disclosure.
Figure 19:
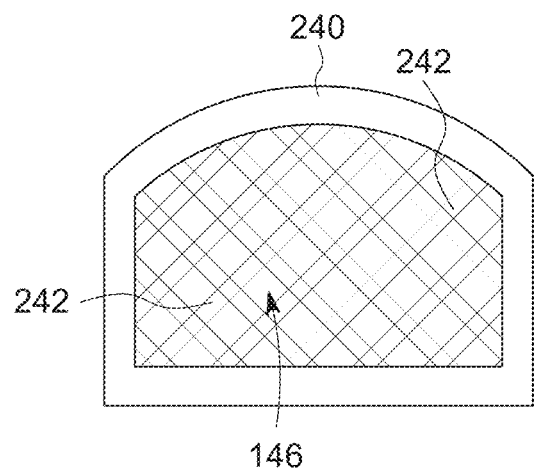
FIG. 19 is a cross-sectional view of the arch member of FIG. 18 taken along line 19-19 in FIG. 18, in accordance with an aspect of the present disclosure.

Referring now to FIGS. 18-19, another arch member 240 of the orthotic device 100 is shown. The arch member 240 may include, for example, a top or superior portion 134, a bottom or inferior portion 136, a first or distal end 138, a second or proximal end 140, a medial side 142, and a lateral side 144, as shown in FIG. 18. The superior portion 134, the inferior portion 136, the distal end 138, the proximal end 140, the medial side 142, and the lateral side 144 are the same or similar to as described above with reference to FIGS. 1-7 and will not be described again here for brevity's sake. The arch member 240 includes arch segments 242 extending through and across the opening 146 of the arch member 240. The arch segments 242 may extend, for example, from the superior portion 134 to the inferior portion 136 and/or from the medial side 142 to the lateral side 144. Further, the arch segments 242 may extend, for example, between any two of the superior portions 134, the inferior portion 136, the medial side 142, and the lateral side 144 at various angles. The arch segments 242 may be made of, for example, pliable soft plastic or the like. The arch segments 242 may, for example, provide additional support to the arch members 240.

As may be recognized by those of ordinary skill in the art based on the teachings herein, numerous changes and modifications may be made to the above-described and other embodiments of the present disclosure without departing from the scope of the disclosure. The components of the device as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices may include more or fewer components or features than the embodiments as described and illustrated herein. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiment. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. An orthotic device, comprising:
a base member;
an arch support portion; and
a covering coupling the arch support portion to the base member;
wherein the arch support portion comprises:
a plurality of arch members surrounded by the covering, wherein each of the arch members is separate and independent from each other arch member; and
a guide portion coupled to the base member and the arch support portion by the covering, wherein the guide portion comprises:
a guide base member; and
a plurality of extensions coupled to and extending from the guide base member;
wherein each extension of the plurality of extensions is positioned between adjacent arch members of the plurality of arch members, wherein the guide base member is positioned only on a medial side of the plurality of arch members, and wherein the plurality of extensions extend from the guide base member toward the base member of the orthotic device from a medial side toward a lateral side of the orthotic device.

2. The orthotic device of claim 1, wherein the base member of the orthotic device comprises:
a superior side; and
an inferior side opposite the superior side.

3. The orthotic device of claim 2, wherein the base member of the orthotic device further comprises:
a medial side; and
a lateral side opposite the medial side,
wherein the medial side includes a recessed region for receiving the arch support portion.

4. The orthotic device of claim 1, wherein each arch member of the plurality of arch members comprises:
a top portion;
a bottom portion opposite the top portion;
a first end;
a second end opposite the first end;
the medial side coupled to the top portion on one end and the bottom portion on another end; and
a lateral side coupled to the top portion on one end and the bottom portion on another end,
wherein each extension of the plurality of extensions is positioned adjacent to at least one of the first end and the second end of a respective arch member of the plurality of arch members.

5. The orthotic device of claim 4, wherein the first end and the second end of each arch member is angled between the medial side and the lateral side.

6. The orthotic device of claim 4, wherein each arch member of the plurality of arch members further comprises:
an opening extending from the first end to the second end.

7. The orthotic device of claim 6, wherein the opening of each arch member of the plurality of arch members comprises:
at least one arch segment extending through the opening.

8. The orthotic device of claim 4, wherein the plurality of arch members are collated within the covering, and wherein the first end of each arch member of the plurality of arch members is positioned next to the second end of each adjacent arch member of the plurality of arch members in a first position.

9. The orthotic device of claim 4, wherein each arch member of the plurality of arch members is positioned at least partially overlapping each adjacent arch member of the plurality of arch members in a second position.

10. The orthotic device of claim 9, wherein the covering is selected from an elastic covering or a deformable covering.

11. The orthotic device of claim 9, wherein the covering is sealed to a rim of the base member positioned in a recessed region of the base member.

12. The orthotic device of claim 1, wherein the plurality of the extensions extend from the guide base member toward the base member perpendicular to a direction from a proximal end to a distal end of the base member and wherein at least one first extension of the plurality of extensions has a different length than at least one second extension of the plurality of extensions.

13. The orthotic device of claim 1, wherein the guide base member is curved between a first end and a second end of the guide base member.

* * * * *